(12) United States Patent
Wang

(10) Patent No.: US 10,489,964 B2
(45) Date of Patent: Nov. 26, 2019

(54) MULTIMODALITY MULTI-AXIS 3-D IMAGING WITH X-RAY

(71) Applicant: LI-COR, Inc., Lincoln, NE (US)

(72) Inventor: Han-Wei Wang, Lincoln, NE (US)

(73) Assignee: LI-COR, INC., Lincoln, NE (US)

(*) Notice: Subject to any disclaimer, the term of this patent is extended or adjusted under 35 U.S.C. 154(b) by 337 days.

(21) Appl. No.: 15/494,088

(22) Filed: Apr. 21, 2017

(65) Prior Publication Data
US 2017/0309063 A1     Oct. 26, 2017

Related U.S. Application Data

(60) Provisional application No. 62/325,588, filed on Apr. 21, 2016.

(51) Int. Cl.
*G06T 15/20* (2011.01)
*G01N 23/04* (2018.01)
(Continued)

(52) U.S. Cl.
CPC .......... *G06T 15/20* (2013.01); *B43K 8/02* (2013.01); *G01N 23/223* (2013.01);
(Continued)

(58) Field of Classification Search
CPC ...... B43K 8/02; G01N 21/1702; G01N 21/31; G01N 21/4795; G01N 21/6456;
(Continued)

(56) References Cited

U.S. PATENT DOCUMENTS 2,792,502 A    5/1957  O'Connor et al.
5,103,338 A    4/1992  Crowley et al.
(Continued)

FOREIGN PATENT DOCUMENTS

CN    101301192    11/2008
CN    102048525     5/2012
(Continued)

OTHER PUBLICATIONS

U.S. Appl. No. 15/192,771, "Final Office Action," dated Jan. 8, 2019, 10 pages.
(Continued)

*Primary Examiner* — Mark R Gaworecki
(74) *Attorney, Agent, or Firm* — Kilpatrick Townsend & Stockton LLP

(57) ABSTRACT

Methods and devices are disclosed for the imaging of a biological sample from all rotational perspectives in three-dimensional space and with multiple imaging modalities. A biological sample is positioned on an imaging stage that is capable of full 360-degree rotation in at least one of two orthogonal axes. Positioned about the stage are imaging modules enabling the recording of a series of images in multiple modalities, including reflected visible light, fluorescence, X-ray, ultrasound, and optical coherence tomography. A computer can use the images to construct three-dimensional models of the sample and to render images of the sample conveying information from one or more imaging channels. The rendered images can be displayed for an operator who can manipulate the images to present additional information or viewing angles of the sample. The image manipulation can be with touch gestures entered using a sterilizable or disposable touch pen.

15 Claims, 8 Drawing Sheets

(51) Int. Cl.
*G06F 3/0484* (2013.01)
*G06F 3/0488* (2013.01)
*B43K 8/02* (2006.01)
*G01N 23/2204* (2018.01)
*G01N 23/223* (2006.01)
*G06F 3/0354* (2013.01)
*G06T 19/00* (2011.01)
*G06T 19/20* (2011.01)

(52) U.S. Cl.
CPC ..... *G01N 23/2204* (2013.01); *G06F 3/03545* (2013.01); *G06F 3/04842* (2013.01); *G06F 3/04845* (2013.01); *G06F 3/04886* (2013.01); *G06T 19/003* (2013.01); *G06T 19/20* (2013.01); *G01N 2223/401* (2013.01); *G01N 2223/408* (2013.01); *G06T 2219/2016* (2013.01)

(58) Field of Classification Search
CPC ............. G01N 23/046; G01N 23/2204; G01N 23/223; G01N 29/0672; G01N 29/225; G01N 29/2418; G01N 2223/401; G01N 2223/408; G06F 3/03545; G06F 3/04842; G06F 3/04845; G06F 3/04886; G06T 15/20; G06T 19/003; G06T 19/20; G06T 2219/2016
See application file for complete search history.

(56) References Cited

U.S. PATENT DOCUMENTS

| | | | |
|---|---|---|---|
| 5,224,141 A | 6/1993 | Yassa et al. |
| 5,408,294 A | 4/1995 | Lam |
| 5,812,265 A | 9/1998 | Hoshiyama |
| 5,959,295 A | 9/1999 | Braun |
| 6,165,170 A | 12/2000 | Wynne et al. |
| 6,172,373 B1 | 1/2001 | Hara et al. |
| 6,356,272 B1 | 3/2002 | Matsumoto et al. |
| RE37,913 E | 11/2002 | Nishi |
| 6,711,433 B1 | 3/2004 | Geiger et al. |
| 7,218,393 B2 | 5/2007 | Sharpe et al. |
| 7,286,232 B2 | 10/2007 | Bouzid et al. |
| 7,453,456 B2 | 11/2008 | Petrov et al. |
| 7,505,124 B2 | 3/2009 | Kreckel et al. |
| 7,551,711 B2 | 6/2009 | Sarment et al. |
| 7,715,523 B2 | 5/2010 | Lafferty et al. |
| 7,929,743 B2 | 4/2011 | Khorasani et al. |
| 8,115,918 B2 | 2/2012 | Zavislan et al. |
| 8,220,415 B2 | 7/2012 | Lamb et al. |
| 8,503,602 B2 | 8/2013 | Lafferty et al. |
| 8,741,232 B2 | 6/2014 | Baysal et al. |
| 8,754,384 B1 | 6/2014 | Persoon et al. |
| 8,851,017 B2 | 10/2014 | Lamb et al. |
| 8,892,192 B2 | 11/2014 | Cuccia et al. |
| 9,053,563 B2 | 6/2015 | Embrey et al. |
| 9,528,938 B2 | 12/2016 | Wang |
| 9,557,281 B2 | 1/2017 | Yang et al. |
| 9,632,187 B2 | 4/2017 | Poon et al. |
| 10,254,227 B2 | 4/2019 | Wang |
| 10,278,586 B2 | 5/2019 | Wang |
| 2003/0078477 A1 | 4/2003 | Kang et al. |
| 2004/0101088 A1 | 5/2004 | Sabol et al. |
| 2005/0046840 A1 | 3/2005 | Kusuzawa et al. |
| 2005/0227374 A1 | 10/2005 | Cunningham et al. |
| 2006/0072123 A1 | 4/2006 | Wilson et al. |
| 2006/0250518 A1 | 11/2006 | Nilson et al. |
| 2006/0253035 A1 | 11/2006 | Stern |
| 2007/0121099 A1 | 5/2007 | Matsumoto et al. |
| 2007/0276184 A1 | 11/2007 | Okawa |
| 2008/0077019 A1 | 3/2008 | Xiao et al. |
| 2008/0297890 A1 | 12/2008 | Natori et al. |
| 2008/0312540 A1 | 12/2008 | Ntziachristos |
| 2009/0011386 A1 | 1/2009 | Eiff et al. |
| 2009/0018451 A1 | 1/2009 | Bai et al. |
| 2009/0032731 A1 | 2/2009 | Kimura et al. |
| 2009/0129543 A1 | 5/2009 | Le Gros et al. |
| 2009/0192358 A1 | 7/2009 | Jaffer et al. |
| 2009/0208072 A1 | 8/2009 | Seibel et al. |
| 2009/0234225 A1 | 9/2009 | Martin et al. |
| 2009/0250631 A1 | 10/2009 | Feke et al. |
| 2010/0309548 A1 | 12/2010 | Power et al. |
| 2011/0116694 A1 | 5/2011 | Gareau et al. |
| 2011/0135190 A1 | 6/2011 | Maad |
| 2011/0229023 A1 | 9/2011 | Jones et al. |
| 2012/0049087 A1 | 3/2012 | Choi et al. |
| 2012/0049088 A1 | 3/2012 | Klose |
| 2012/0065518 A1 | 3/2012 | Mangoubi et al. |
| 2012/0105600 A1 | 5/2012 | Meyer et al. |
| 2012/0182411 A1 | 7/2012 | Nakatsuka et al. |
| 2012/0194663 A1 | 8/2012 | Haisch et al. |
| 2012/0206577 A1 | 8/2012 | Guckenberger et al. |
| 2012/0302880 A1 | 11/2012 | Tian et al. |
| 2012/0312957 A1 | 12/2012 | Loney et al. |
| 2013/0027516 A1 | 1/2013 | Hart et al. |
| 2013/0135081 A1 | 5/2013 | Mccloskey et al. |
| 2014/0125790 A1 | 5/2014 | Mackie et al. |
| 2014/0140594 A1 | 5/2014 | Mahadevan-Jansen et al. |
| 2014/0163388 A1 | 6/2014 | Sasayama et al. |
| 2014/0276008 A1 | 9/2014 | Steinbach et al. |
| 2014/0294247 A1 | 10/2014 | Sirault et al. |
| 2014/0346359 A1 | 11/2014 | Holliday |
| 2014/0349337 A1 | 11/2014 | Dasari et al. |
| 2014/0378843 A1 | 12/2014 | Valdes et al. |
| 2015/0000410 A1 | 1/2015 | Grimard et al. |
| 2015/0008337 A1 | 1/2015 | Shimizu |
| 2015/0022824 A1 | 1/2015 | Babayoff |
| 2015/0062153 A1 | 3/2015 | Mihalca et al. |
| 2015/0073213 A1 | 3/2015 | Khait et al. |
| 2015/0098126 A1 | 4/2015 | Keller et al. |
| 2015/0105283 A1 | 4/2015 | Hollman-Hewgley et al. |
| 2015/0359413 A1 | 12/2015 | David |
| 2016/0187199 A1 | 6/2016 | Brunk et al. |
| 2016/0245753 A1 | 8/2016 | Wang |
| 2016/0377545 A1 | 12/2016 | Wang |
| 2017/0059487 A1 | 3/2017 | Wang |
| 2017/0176338 A1 | 6/2017 | Wu et al. |
| 2017/0336706 A1 | 11/2017 | Wang |
| 2017/0367582 A1 | 12/2017 | Wang |
| 2018/0020920 A1 | 1/2018 | Ermilov et al. |
| 2018/0140197 A1 | 5/2018 | Wang et al. |
| 2018/0180550 A1 | 6/2018 | Franjic et al. |
| 2019/0079010 A1 | 3/2019 | Bawendi et al. |

FOREIGN PATENT DOCUMENTS

| | | |
|---|---|---|
| CN | 103082997 | 10/2015 |
| DE | 102011104216 | 12/2012 |
| EP | 2455891 | 5/2012 |
| GB | 2514125 | 11/2014 |
| JP | 02304366 A | 12/1990 |
| JP | 09236755 A | 9/1997 |
| JP | 10123054 A | 5/1998 |
| JP | 2004531729 A | 10/2004 |
| KR | 20130096910 | 9/2013 |
| WO | 2006113908 | 10/2006 |
| WO | 2007030424 | 3/2007 |
| WO | 2009115061 | 9/2009 |
| WO | 2013166497 | 11/2013 |
| WO | 2014094142 | 6/2014 |
| WO | 2015023990 | 2/2015 |
| WO | 2016014252 | 1/2016 |
| WO | 2016073569 | 5/2016 |
| WO | 2016100214 | 6/2016 |
| WO | 2016137899 | 9/2016 |
| WO | 2016210340 | 12/2016 |
| WO | 2017184940 | 10/2017 |
| WO | 2017200801 | 11/2017 |
| WO | 2017223378 | 12/2017 |
| WO | 2018098162 | 5/2018 |

OTHER PUBLICATIONS

(56) References Cited

OTHER PUBLICATIONS

U.S. Appl. No. 15/630,776, "Notice of Allowance," dated Dec. 21, 2018, 7 pages.
EP16756129.9, "Extended European Search Report," dated Jan. 29, 2019, 14 pages.
EP16815434.2, "Partial Supplementary European Search Report," dated Jan. 29, 2019, 16 pages.
PCT/US2017/038860, "International Preliminary Report on Patentability," dated Jan. 3, 2019, 8 pages.
U.S. Appl. No. 15/352,427, "Notice of Allowance," dated Nov. 21, 2018, 6 pages (not attached).
EP16756129.9, "Partial European Search Report," dated Oct. 29, 2018, 17 pages.
Orpheus Medical, Clinical Video Management and Visible Light Documentation, Slideshow dated Feb. 3, 2016. The Examiner's attention is directed to slide 11.
U.S. Appl. No. 15/352,427, Non-Final Office Action, dated Sep. 4, 2018, 9 pages.
U.S. Appl. No. 15/192,771, "Notice of Allowance", dated Apr. 2, 2019, 8 pages.
U.S. Appl. No. 15/955,567, "Notice of Allowance", dated Apr. 2, 2019, 11 pages.
"Arctec Eva Fast Handheld 3D Scanner for Professionals", http://www.artec3d.com/hardware/artec-eva, retrieved from the internet Apr. 19, 2016, 6 pages.
Bioptics Inc., "BioVision Digital Specimen Radiography (DSR) System", Premarket Notification 510(k) Summary, prepared May 2009, 8 pages.
Fang et al., "Combined Optical and X-ray Tomosynthesis Breast Imaging", Radiology, vol. 258, No. 1, Jan. 2011, pp. 89-97.
Faxitron Bioptics LLC, "BioVision Surgical Specimen Radiography System", http://www.faxitron.com/medical/products/biovision.html, retrieved from the internet on Apr. 26, 2016, 2 pages.
Faxitron Bioptics LLC, "Path Vision", http://www.faxitron.com/medical/products/pathvision.html, retrieved from the internet on Apr. 26, 2016, 2 pages.
Lamberts et al., "Tumor-specific uptake of fluorescent bevacizumab-IRDye800CW microdosing in patients with primary breast cancer: a phase I feasibility study", Clinical Cancer Research, Personalized Medicine and Imaging, American Association for Cancer Research, 2016, 41 pages.
International Search Report and Written Opinion dated Jun. 23, 2016 for PCT/US2016/018972, 10 pages.
International Search Report and Written Opinion dated Sep. 13, 2016 for PCT/US2016/039382, 14 pages.
Tomowave Laboratories, "Imaging Modules", retrieved from the internet: http://www.tomowave.com/imagingmodules.html, 2005, 1 page.
Wu et al., "Rotational imaging optical coherence tomography for full-body mouse embryonic imaging", Journal of Biomedical Optics, vol. 21, No. 2, Feb. 2016, pp. 026002-1-026002-9.
International Search Report for PCT/US2018/027978, dated Jul. 12, 2018, 5 pages.
Sturm et al., "CopyMe3D: Scanning and Printing Persons in 30*", Medical Image Computing and Computer-Assisted Intervention—Miccai 2015: 18th International Conference, Munich, Germany, Sep. 3, 2013, pp. 405-414.
International Search Report dated Feb. 8, 2018 for PCT Appln No. PCT/US2017/062812, 4 pages.
U.S. Appl. No. 15/049,970, "Notice of Allowability", dated Oct. 14, 2016, 4 pages.
EP16815434.2, "Extended European Search Report", dated May 16, 2019, 18 pages.
JP2017-544296, "Office Action", dated May 7, 2019, 5 pages.
PCT/US2016/018972, "International Preliminary Report on Patentability", dated Aug. 29, 2017, 7 pages.
PCT/US2017/062812, "International Preliminary Report on Patentability", dated Jun. 6, 2019, 7 pages.
Kleiner et al., "Classification of Ambiguous Nerve Fiber Orientations in 3D Polarized Light Imaging", Med Image Comput Comput Assist Interv., vol. 15, Pt 1, 2012, pp. 206-213.
Lee et al., "Fusion of coregistered cross-modality images using a temporally alternating display method", Medical & Biological Engineering & Computing, Springer, vol. 38, No. 2, Mar. 1, 2000, pp. 127-132.
International Search Report and Written Opinion dated Sep. 22, 2017 for PCT/US2017/028769, 19 pages.
International Search Report and Written Opinion dated Sep. 19, 2017 for PCT/US2017/031740, 25 pages.
International Search Report and Written Opinion dated Sep. 22, 2017 for PCT/US2017/038860, 13 pages.

MULTIMODALITY MULTI-AXIS 3-D IMAGING WITH X-RAY

CROSS-REFERENCES TO RELATED APPLICATIONS

This application claims the benefit of U.S. Provisional Application No. 62/325,588, filed Apr. 21, 2016, which is incorporated in its entirety herein for all purposes.

STATEMENT AS TO RIGHTS TO INVENTIONS MADE UNDER FEDERALLY SPONSORED RESEARCH AND DEVELOPMENT

Not applicable

BACKGROUND

Assessment of tumor margin during surgery is essential to the optimal outcome of many oncologic procedures. Tumor margins are the healthy tissue surrounding the tumor, more specifically, the distance between the tumor tissue and the edge of the surrounding tissue removed along with the tumor. Ideally, the margins are selected so that the risk of leaving tumor tissue within the patient is low.

Fluorescence image-guided systems can be used in conjunction with a series of imaging agents to visualize tumor margins during surgical procedures for cancer removal. However, in many cancer surgeries deep surgical cavities with closed spaces and hidden linings pose significant challenges for the use of over-head imaging systems. This is particularly true for breast-conserving surgeries and treatments of head and neck cancers. Discharging bio-fluids and small fields of view also can compromise the utility of handheld fluorescence devices for margin assessment at the surgical cavity. Therefore, intraoperative diagnosis on resected surgical samples promises to be a more effective means for margin assessment in many surgical cancer treatment applications.

BRIEF SUMMARY

In general, provided herein are devices and methods for imaging with multiple imaging modalities to provide views of the sample from positions distributed about the sample in any three-dimensional rotational direction. The sample is positioned on an imaging stage that is transparent to visible light, near-infrared light, X-rays, or other types of radiation relevant to the imaging modalities being used. The imaging stage is fully rotatable in any direction, so that cameras, detectors, or sensors located at positions about the stage can record images of the sample taken from multiple angles. Because the imaging stage is transparent, these images of the sample can be recorded through the stage itself.

Typical imaging modalities used include full-color or black-and-white imaging of the sample with cameras that record reflected visible light, and fluorescence imaging with cameras that record regions of the sample that fluoresce when illuminated at an excitation frequency. This fluorescence can be associated with dyes that have binding affinity for diseased cells to be surgically removed. Other imaging modalities that can be used include X-ray imaging to visualize tissue density and radiopaque tissue inserts, photoacoustic imaging, thermoacoustic imaging, ultrasonic imaging, and optical coherence tomography (OCT).

A display device can be used to present images rendered using information recorded in each of the multiple imaging modalities. The presentation can simultaneously or sequentially display images from multiple modalities or from multiple angles relative to the sample. This multimodal and multi-axis imaging can, for example, offer a novel way to visualize resected tissue samples, providing surgeons with an improved understanding of tumor outlines and tissue characteristics.

One provided apparatus for imaging a biological sample with visible light, fluorescence, and X-rays, comprises a rotatable imaging stage adapted for supporting at least a portion of a biological sample within an imaging volume. The rotatable imaging stage has a first rotational axis and a second rotational axis. The second rotational axis is orthogonal to the first rotational axis. The apparatus further comprises an X-ray source configured to irradiate the imaging volume with X-rays, an X-ray imager configured to detect X-rays exiting the imaging volume, a fluorescence excitation light source configured to illuminate the imaging volume, a first camera configured to have a depth of focus within the imaging volume and to detect reflected light, and a second camera configured to have a depth of focus within the imaging volume and to detect fluorescence.

In some embodiments, the imaging stage comprises a transparent portion that is transparent to visible light and near-infrared light. In some embodiments, the transparent portion is transparent to X-rays. In some embodiments, the transparent portion comprises glass or acrylic. In some embodiments the imaging stage comprises a plurality of marks at predetermined intervals, wherein the marks comprise a radiopaque material. In some embodiments, the radiopaque material comprises a metal.

In some embodiments, the X-ray source is an X-ray tube. In some embodiments, the X-ray imager is a flat panel detector. In some embodiments, the first camera is the second camera.

In some embodiments, the apparatus further comprises a computer processor operatively connected with a machine-readable non-transitory medium embodying information indicative of instructions for causing the computer processor to perform operations. In some embodiments, the computer processor records reflected light images of the biological sample using the first camera. In some embodiments, the computer processor records fluorescence images of the biological sample using the second camera. In some embodiments, the computer processor records X-ray images of the biological sample using the X-ray imager. In some embodiments, the computer processor rotates the rotatable imaging stage around at least one of the first rotational axis and the second rotational axis.

In some embodiments, the computer processor constructs a three-dimensional reflected light model from two or more reflected light images, wherein each of the two or more reflected light images is recorded with the rotatable imaging stage oriented in different positions around at least one of the first rotational axis and the second rotational axis. In some embodiments, the computer processor constructs a three-dimensional fluorescence model from two or more fluorescence images, wherein each of the two or more fluorescence images is recorded with the rotatable imaging stage oriented in different positions around at least one of the first rotational axis and the second rotational axis. In some embodiments, the computer processor constructs a three-dimensional X-ray model from two or more X-ray images, wherein each of the two or more X-ray images is recorded with the rotatable imaging stage oriented in different positions around at least one of the first rotational axis or the second rotational axis. In some embodiments, the computer processor renders an image produced from the reflected light model, the fluorescence model, and the X-ray model, wherein the reflected light model, the fluorescence model, and the X-ray model are identically registered in three-dimensional space.

Also provided is an apparatus for imaging a biological sample with visible light, fluorescence, and ultrasound, comprising a rotatable imaging stage adapted for supporting at least a portion of a biological sample within an imaging volume. The rotatable imaging stage comprises a first rotational axis and a second rotational axis. The second rotational axis is orthogonal to the first rotational axis. The apparatus further comprises an energy source configured to transmit energy pulses into the imaging volume, an ultrasonic transducer array configured to detect ultrasonic emissions exiting the imaging volume, a fluorescence excitation light source configured to illuminate the imaging volume, a first camera configured to have a depth of focus within the imaging volume and to detect reflected light, and a second camera configured to have a depth of focus within the imaging volume and to detect fluorescence.

In some embodiments, the energy pulses are non-ionizing laser pulses. In some embodiments, the energy pulses are radio frequency pulses. In some embodiments, the energy pulses are ultrasonic pulses.

In some embodiments, the imaging stage comprises a transparent portion that is transparent to visible light and near-infrared light. In some embodiments, the imaging stage comprises a plurality of marks at predetermined intervals. In some embodiments, the first camera is the second camera.

In some embodiments, the apparatus further comprises a computer processor operatively connected with a machine-readable non-transitory medium embodying information indicative of instructions for causing the computer processor to perform operations. In some embodiments, the computer processor records reflected light images of the biological sample using the first camera. In some embodiments, the computer processor records fluorescence images of the biological sample using the second camera. In some embodiments, the computer processor records ultrasound images of the biological sample using the ultrasonic transducer array. In some embodiments, the computer processor rotates the rotatable imaging stage around at least one of the first rotational axis and the second rotational axis.

In some embodiments, the computer processor constructs a three-dimensional reflected light model from two or more reflected light images, wherein each of the two or more reflected light images is recorded with the rotatable imaging stage oriented in different positions around at least one of the first rotational axis and the second rotational axis. In some embodiments, the computer processor constructs a three-dimensional fluorescence model from two or more fluorescence images, wherein each of the two or more fluorescence images is recorded with the rotatable imaging stage oriented in different positions around at least one of the first rotational axis and the second rotational axis. In some embodiments, the computer processor constructs a three-dimensional ultrasonic model from two or more ultrasound images, wherein each of the two or more ultrasound images is recorded with the rotatable imaging stage oriented in different positions around at least one of the first rotational axis or the second rotational axis. In some embodiments, the computer processor renders an image produced from the reflected light model, the fluorescence model, and the ultrasonic model, wherein the reflected light model, the fluorescence model, and the ultrasonic model are identically registered in three-dimensional space.

Also provided is an apparatus for imaging a biological sample with visible light, fluorescence, and optical coherence tomography, comprising a rotatable imaging stage adapted for supporting at least a portion of a biological sample within an imaging volume. The rotatable imaging stage has a first rotational axis and a second rotational axis. The second rotational axis is orthogonal to the first rotational axis. The apparatus further comprises a near-infrared light source configured to transmit near-infrared light into the imaging volume, a fluorescence excitation light source configured to illuminate the imaging volume, a first camera configured to have a depth of focus within the imaging volume and to detect reflected light, a second camera configured to have a depth of focus within the imaging volume and to detect fluorescence, and a third camera configured to have a depth of focus within the imaging volume and to detect near-infrared light.

In some embodiments, the imaging stage comprises a transparent portion that is transparent to visible light and near-infrared light. In some embodiments, the imaging stage comprises a plurality of marks at predetermined intervals. In some embodiments, the first camera is the second camera.

In some embodiments, the apparatus further comprises a computer processor operatively connected with a machine-readable non-transitory medium embodying information indicative of instructions for causing the computer processor to perform operations. In some embodiments, the computer processor records reflected light images of the biological sample using the first camera. In some embodiments, the computer processor records fluorescence images of the biological sample using the second camera. In some embodiments, the computer processor records optical coherence tomography images of the biological sample using the third camera. In some embodiments, the computer processor rotates the rotatable imaging stage around at least one of the first rotational axis and the second rotational axis.

In some embodiments, the computer processor constructs a three-dimensional reflected light model from two or more reflected light images, wherein each of the two or more reflected light images is recorded with the rotatable imaging stage oriented in different positions around at least one of the first rotational axis and the second rotational axis. In some embodiments, the computer processor constructs a three-dimensional fluorescence model from two or more fluorescence images, wherein each of the two or more fluorescence images is recorded with the rotatable imaging stage oriented in different positions around at least one of the first rotational axis and the second rotational axis. In some embodiments, the computer processor constructs a three-dimensional optical coherence tomography model from two or more optical coherence tomography images, wherein each of the two or more optical coherence tomography images is recorded with the rotatable imaging stage oriented in different positions around at least one of the first rotational axis or the second rotational axis. In some embodiments, the computer processor renders an image produced from the reflected light model, the fluorescence model, and the optical coherence tomography model, wherein the reflected light model, the fluorescence model, and the optical coherence tomography model are identically registered in three-dimensional space.

Also provided is a sterile touch pen comprising a pen body and a pen tip. The pen tip is attached to an end of the pen body. In some embodiments, the pen tip is a touch tip, the end of the pen body is a first end, and the touch pen further comprises an ink tip configured to dispense ink, wherein the ink tip is attached to a second end of the pen body, and wherein the second end is opposite to the first end.

In some embodiments, the ink comprises a fluorescent dye. In some embodiments, the pen body comprises stainless steel. In some embodiments, the pen tip is detachable from the pen body and replaceable with a second pen tip. In some embodiments, the touch pen further comprises a pen cover. The pen cover encloses the pen body and the pen tip, and is sterile.

Also provided is a method for imaging a biological sample with visible light, fluorescence and X-rays. The method comprises illuminating a biological sample within an imaging volume on a rotatable imaging stage with visible light. The rotatable imaging stage has a first rotational axis, a second rotational axis, and a transparent portion. The second rotational axis is orthogonal to the first rotational axis. The transparent portion is transparent to visible light, near-infrared light, and X-rays. The method further comprises recording, using a first camera, a first reflected light image of visible light reflected by the biological sample. The method further comprises illuminating the biological sample on the rotatable imaging stage with fluorescence excitation light using a fluorescence excitation light source. The method further comprises recording, using a second camera, a first fluorescence image of fluorescence emission light emitted by the biological sample. The method further comprises irradiating the biological sample on the rotatable imaging stage with X-rays using an X-ray source. The method further comprises recording, using an X-ray imager, a first X-ray image of the X-rays exiting the imaging volume. The method further comprises rotating the imaging stage by a predetermined amount around at least one of the first rotational axis and the second rotational axis. The method further comprises recording a second reflected light image of visible light reflected by the biological sample through the transparent portion of the rotatable imaging stage. The method further comprises illuminating the biological sample with fluorescence excitation light. The method further comprises recording a second fluorescence image of fluorescence emission light emitted by the biological sample through the transparent portion of the rotatable imaging stage. The method further comprises irradiating the biological sample with X-rays. The method further comprises recording a second X-ray image of the X-rays exiting the imaging volume through the transparent portion of the rotatable imaging stage.

In some embodiments, the method further comprises constructing a three-dimensional reflected light model from the first and second reflected light images using a computer. In some embodiments, the method further comprises constructing a three-dimensional fluorescence model from the first and second fluorescence images using the computer. In some embodiments, the method further comprises constructing a three-dimensional X-ray model from the first and second X-ray images using the computer. In some embodiments, the method further comprises rendering an image produced from the reflected light model, the fluorescence model, and the X-ray model, wherein the reflected light model, the fluorescence model, and the X-ray model are identically registered in three-dimensional space.

In some embodiments, the method further comprises positioning the X-ray imager between the biological sample and the camera. In some embodiments, the X-ray imager is a flat panel detector. In some embodiments, the flat panel detector has a detection face and a display face, wherein the display face is opposite to the detection face, wherein the detection face is directed towards the biological sample, and wherein the display face is directed towards the camera. In some embodiments, the method further comprises irradiating the biological sample on the rotatable imaging stage with X-rays using an X-ray source, wherein the biological sample is positioned between the X-ray source and the flat panel detector, and wherein the X-ray source, the biological sample, the flat panel detector, and the first camera are collinear. In some embodiments, the method further comprises converting the X-rays detected by the detection face of the flat panel detector into a first X-ray image displayed on the display face of the flat panel detector. In some embodiments, the method further comprises recording using the first camera the first X-ray image displayed on the display face of the flat panel detector. In some embodiments, the method further comprises positioning the flat panel detector such that the flat panel detector is not between the biological sample and the camera. In some embodiments, the method further comprises rotating the imaging stage by a predetermined amount around at least of the first rotational axis and the second rotational axis. In some embodiments, the method further comprises positioning the flat panel detector between the biological sample and the camera. In some embodiments, the method further comprises irradiating the biological sample on the rotatable imaging stage with X-rays using an X-ray source. In some embodiments, the method further comprises converting the X-rays detected through the transparent portion of the rotatable imaging stage by the detection face of the flat panel detector into a second X-ray image displayed on the display face of the flat panel detector. In some embodiments, the method further comprises recording, using the first camera, the second X-ray image displayed on the display face of the X-ray flat panel detector.

Also provided is a method for imaging a biological sample with visible light, fluorescence, and ultrasound. The method comprises illuminating a biological sample within an imaging volume on a rotatable imaging stage with visible light. The rotatable imaging stage has a first rotational axis, a second rotational axis, and a transparent portion. The second rotational axis is orthogonal to the first rotational axis. The transparent portion is transparent to visible light and near-infrared light. The method further comprises recording using a first camera a first reflected light image of visible light reflected by the biological sample. The method further comprises illuminating the biological sample on the rotatable imaging stage with fluorescence excitation light using a fluorescence excitation light source. The method further comprises recording using a second camera a first fluorescence image of fluorescence emission light emitted by the biological sample. The method further comprises transmitting energy pulses into the biological sample, wherein the energy pulses are absorbed by the biological sample and converted into ultrasonic emissions. The method further comprises detecting the ultrasonic emissions using an ultrasonic transducer array. The method further comprises recording a first ultrasound image constructed from the ultrasonic emissions detected by the ultrasonic transducer array. The method further comprises rotating the imaging stage by a predetermined amount around at least one of the first rotational axis and the second rotational axis. The method further comprises recording a second reflected light image of visible light reflected by the biological sample through the transparent portion of the rotatable imaging stage. The method further comprises illuminating the biological sample with fluorescence excitation light. The method further comprises recording a second fluorescence image of fluorescence emission light emitted by the biological sample through the transparent portion of the rotatable imaging stage. The method further comprises transmitting energy pulses into the biological sample, wherein the energy pulses are absorbed by the biological sample and converted into ultrasonic emissions. The method further comprises detecting the ultrasonic emissions using an ultrasonic transducer array. The method further comprises recording a second ultrasound image constructed from the ultrasonic emissions detected by the ultrasonic transducer array.

In some embodiments, the method further comprises constructing a three-dimensional reflected light model from the first and second reflected light images using a computer. In some embodiments, the method further comprises constructing a three-dimensional fluorescence model from the first and second fluorescence images using the computer. In some embodiments, the method further comprises constructing a three-dimensional ultrasonic model from the first and second ultrasound images using the computer. In some embodiments, the method further comprises rendering an image produced by overlaying the reflected light model, the fluorescence model, and the ultrasonic model, wherein the reflected light model, the fluorescence model, and the ultrasonic model are identically registered in three-dimensional space.

In some embodiments, the energy pulses are non-ionizing laser pulses and the ultrasound image is a photoacoustic image. In some embodiments, the energy pulses are radio frequency pulses and the ultrasound image is a thermoacoustic image. In some embodiments, the energy pulses are ultrasonic pulses.

Also provided is a method for imaging a biological sample with visible light, fluorescence, and optical coherence tomography. The method comprises illuminating a biological sample within an imaging volume on a rotatable imaging stage with visible light. The rotatable imaging stage has a first rotational axis, a second rotational axis, and a transparent portion. The second rotational axis is orthogonal to the first rotational axis. The transparent portion is transparent to visible light and near-infrared light. The method further comprises recording using a first camera a first reflected light image of visible light reflected by the biological sample. The method further comprises illuminating the biological sample on the rotatable imaging stage with fluorescence excitation light using a fluorescence excitation light source. The method further comprises recording using a second camera a first fluorescence image of fluorescence emission light emitted by the biological sample. The method further comprises illuminating the biological sample on the rotatable imaging stage with near-infrared light. The method further comprises recording using a third camera a first optical coherence tomography image of near-infrared light reflected by the biological sample. The method further comprises rotating the imaging stage by a predetermined amount around at least one of the first rotational axis and the second rotational axis. The method further comprises recording a second reflected light image of visible light reflected by the biological sample through the transparent portion of the rotatable imaging stage. The method further comprises illuminating the biological sample with fluorescence excitation light. The method further comprises recording a second fluorescence image of fluorescence emission light emitted by the biological sample through the transparent imaging stage. The method further comprises illuminating the biological sample with near-infrared light. The method further comprises recording a second optical coherence tomography image of near-infrared light reflected by the biological sample In some embodiments, the method further comprises constructing a three-dimensional reflected light model from the first and second reflected light images using a computer. In some embodiments, the method further comprises constructing a three-dimensional fluorescence model from the first and second fluorescence images using the computer. In some embodiments, the method further comprises constructing a three-dimensional optical coherence tomography model from the first and second optical coherence tomography images using the computer. In some embodiments, the method further comprises rendering an image produced from the reflected light model, the fluorescence model, and the optical coherence tomography model, wherein the reflected light model, the fluorescence model, and the optical coherence tomography model are identically registered in three-dimensional space.

In some embodiments, the second camera is the first camera.

Also provided is a method of presenting to an operator an image on a two-dimensional display. The method comprises displaying on the two-dimensional display an image. The image is a view of a subject from a viewpoint. The subject has a first rotational axis and a second rotational axis. The second rotational axis is orthogonal to the first rotational axis. The method further comprises changing the displayed image to a view of the subject from a viewpoint that is closer to the subject in response to a zoom command by the operator. The method further comprises changing the displayed image to a view of the subject from a viewpoint that is farther from the subject in response to a pinch command by the operator. The method further comprises changing the displayed image to a view of the subject from a viewpoint that is rotated around the first rotational axis in response to a first rotational command by the operator. The method further comprises changing the displayed image to a view of the subject from a viewpoint that is rotated around the second rotational axis in response to a second rotational command by the operator. The method further comprises displaying information associated with at least a portion of the displayed image in response to a selection command by the operator.

In some embodiments, the image is produced from two or more three-dimensional models. In some embodiments, the models are each constructed from two or more images of the subject, and are each identically registered in three-dimensional space.

In some embodiments one or more of the zoom, pinch, rotational, or selection commands are entered using key presses, control sticks, touch gestures, voice activation, or accelerometers.

In some embodiments, the touch gestures are entered using a touch pen. The touch pen comprises a pen body and a pen tip. The pen tip is attached to an end of the pen body. In some embodiments, the pen tip is a touch tip, the end of the pen body is a first end, and the touch pen further comprises an ink tip configured to dispense ink, wherein the ink tip is attached to a second end of the pen body, and wherein the second end is opposite to the first end. In some embodiments, the ink comprises a fluorescent dye. In some embodiments, the touch pen is sterile. In some embodiments, the pen body comprises stainless steel. In some embodiments, the pen tip is detachable from the pen body and replaceable with a second pen tip. In some embodiments, the touch pen further comprises a pen cover, wherein the pen cover encloses the pen body and the pen tip, and wherein the pen cover is sterile.

DETAILED DESCRIPTION

The present invention relates in part to multimodal and multi-axis three-dimensional imaging devices and methods for visualizing samples. The devices and methods can be used to record and display multimodal images of a biological sample representing views of the sample from any position rotated about the sample in three-dimensional space.

A technical advantage of the embodiments described herein is that a surgeon can have enhanced access to visualized information regarding the location and characteristics of diseased and healthy cells and tissue within a resected biopsy sample. This can allow a surgeon to more accurately assess tumor margins during surgical procedures, which can in turn increase the probability of a successful surgery and the survival rate of the patient.

By combining multi-axis rotation three-dimensional imaging with multiple imaging modalities, the inventors have made the surprising discovery of a novel way to look at a resected tissue sample. For example, by combining reflected visible light imaging and fluorescence imaging with an X-ray imaging module, one embodiment of the system describe herein provides three-dimensional full-rotation surface mapping together with X-ray projections from different angles. This can give a surgeon a unique and comprehensive understanding of the molecular signal from a tumor tissue from the optical channels together with tomographic information from the X-ray channel. The optical channels give the molecular signal of a tumor and the outline of the tissue, and the X-ray channel shows the tissue density and projection, as well as information about any metal or wire inserts placed inside the tissue. In some cases, with a molecular probe that gives contrast in multiple channels, such as the fluorescence and X-ray channels, an overlay image of the multimodalities can show signals from the same imaging agent.

Figure 1:
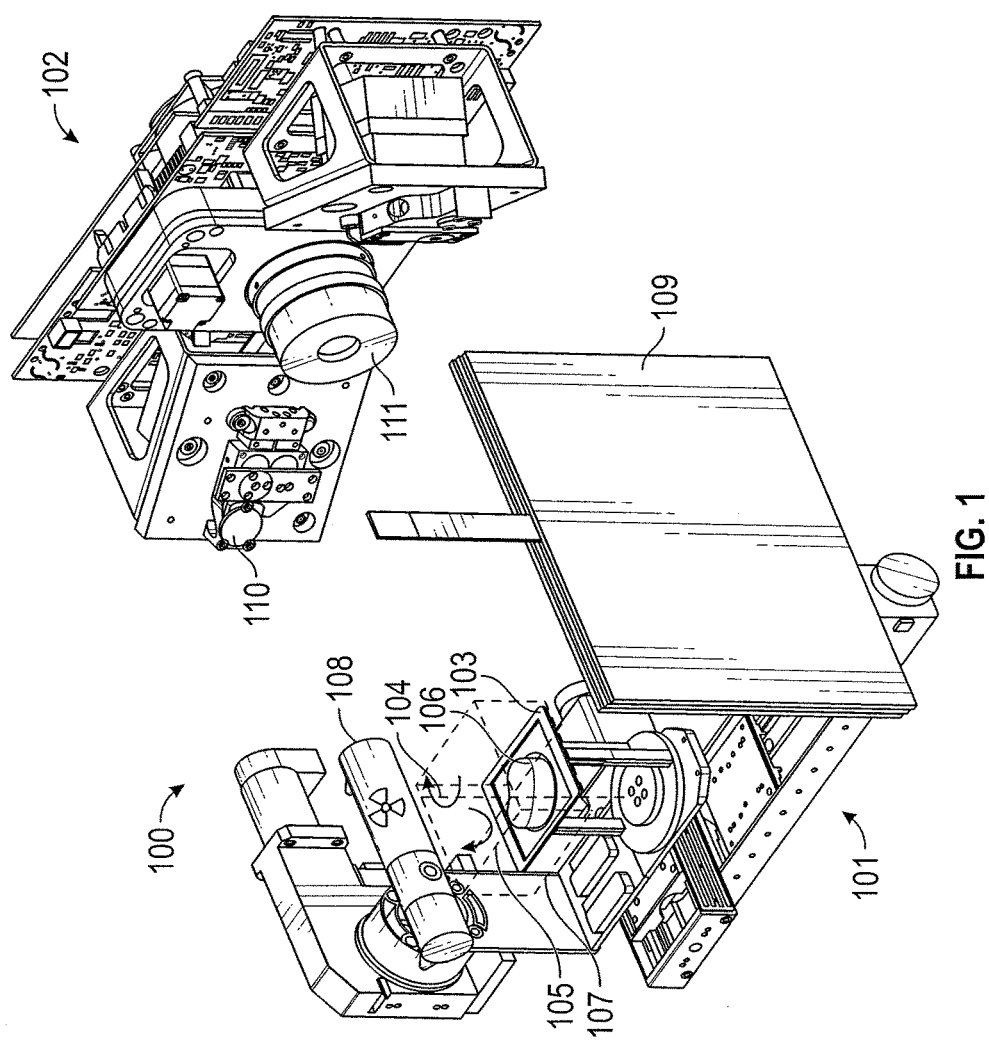
FIG. 1 is a perspective illustration of a rotatable stage and X-ray imaging system in accordance with an embodiment.

FIG. 1 illustrates one embodiment as a descriptive example. Shown is an apparatus 100 comprising a sample positioning module 101 and an optical imaging module 102. The sample positioning module has an imaging stage 103 that has a first rotational axis 104 and a second rotational axis 105. A biological sample 106 is shown being supported by the imaging stage 103. The biological sample 106 is within an imaging volume 107 proximate to the imaging stage 103. An X-ray source 108 is configured to irradiate the imaging volume 107 with X-rays, and an X-ray imager 109 is configured to detect X-rays exiting the imaging volume 107. The optical imaging module 102 has a fluorescence excitation light source 110 configured to illuminate the imaging volume 107, and a camera 111 configured to have a depth of focus within the imaging volume.

The biological sample can comprise material removed from a subject. The subject is typically a human, but also can be another animal. The subject can be, for example, rodent, canine, feline, equine, ovine, porcine, or another primate. The subject can be a patient suffering from a disease. In some embodiments, the subject is a cancer patient. In certain aspects, the biological sample comprises a tumor, such as tumor tissue or cells. In certain aspects, the biological sample comprises a peripheral biopsy of a tissue sample previously removed. In another aspect, the biological sample is tumor tissue such as a breast core biopsy. The biological sample size can be as small as a tissue slice.

The rotatable imaging stage supporting the biological sample is equipped with rotational motors and stages to control the view angle and position of a sample within the imaging volume. By rotating a sample in two degrees of freedom, the stage can allow an imager to efficiently provide a full-rotation three-dimensional image. A first rotational axis can, for example, provide 360-degree movement along the z-axis (roll) relative to the sample. A second rotational axis can, for example, move along the y-axis (tilt) for imaging at different perspectives. Tilting of the sample stage also allows projection views from the top and the bottom of the sample via a transparent window. In some embodiments, the rotational imaging stage can also be moved in an X-Y plane to allow for the registration of the sample to the center of the imaging volume.

Rotational combinations can allow the entire sample to be imaged. To collect pertinent imaging projections along a sample for subsequent three-dimensional reconstruction, the rotational imaging stage can rotate the object in rolling and tilting degrees of freedom. In some embodiments, to provide comprehensive coverage of sample features the rolling angle is in the range of from 7.5 degrees to 30 degrees, depending on the complexity of the sample. In some embodiments, a rolling angle of 22.5 degrees and a tilting angle of ±35 degrees offers a full rotation for three-dimensional inspection and imaging of the sample.

Rotation of the imaging stage around one or both of the first and second rotational axis can be accomplished through the use of rotor bearings connected to the stage. A rotor bearing can be a hub, axle, or other mechanical element that bears contact between at least two parts and that allows for rotation around an axis. A rotary bearing can include circular tracks and cages for ball bearings, lubricant surfaces, and other friction-reducing implements.

The imaging volume is defined as the volume formed by the fields of illumination or other electromagnetic radiation, by the depth-of-focus of an object lens, and by the field-of-view of an imaging head. The imaging volume is typically configured such that all cameras, detectors, sensors, and other image capturing elements of the apparatus are tolerant of placement of the sample anywhere within the volume.

The X-ray source can be any artificial X-ray source configured to irradiate the imaging volume with X-rays. In some embodiments, the X-ray source is an X-ray tube. The X-ray tube can comprise a rotating anode tube. In some embodiments, the X-ray source is a solid-anode microfocus X-ray tube or a metal-jet-anode microfocus X-ray tube.

The X-ray imager can be any device configured to measure the properties of X-rays exiting the image volume. The X-ray imager can comprise, for example, one or more of a sensitized photographic plate, sensitized photographic film, a photostimulable phosphor plate, a semiconductor or solid state detector, or a scintillator. In some embodiments, the X-ray imager comprises a scintillator. The scintillator can comprise any material that converts an X-ray photon to a visible light photon. The scintillator can comprise one or more organic or inorganic compounds. The scintillator compounds can comprise, for example, barium fluoride, calcium fluoride doped with europium, bismuth germinate, cadmium tungstate, cesium iodide doped with thallium, cesium iodide doped with sodium, undoped cesium iodide, gadolinium oxysulfide, lanthanum bromide doped with cerium, lanthanum chloride doped with cerium, lead tungstate, lutetium iodide, lutetium oxyorthosilicate, sodium iodide doped with thallium, yttrium aluminum garnet, zinc sulfide, or zinc tungstate. In some embodiments, the scintillator comprises sodium iodide, gadolinium oxysulfide, or cesium iodide.

In some embodiments, the X-ray imager is a an X-ray flat panel detector. The flat panel detector can comprise a scintillator material and a photodiode transistor array. The flat panel detector can further comprise one or more readout circuits. The flat panel detector can comprise a detection face and a display face on opposite sides of the detector from one another. The detection face can be directed towards the biological sample and the X-ray source so as to be contacted with X-rays generated by the X-ray source and passing through the imaging volume. The display face can be directed towards a camera so that an X-ray image displayed on the display face can be recorded using the camera. In some embodiments, the X-ray image is displayed on the display face by generating visible light that is recorded by a visible light camera configured to have a depth of focus that corresponds to the distance between the display face and the camera.

In preferred embodiments, the X-ray source, biological sample, and X-ray imager are collinear with one another. In this configuration, the X-ray imager can record information related to X-rays that are generated by the X-ray source, travel through the imaging volume, and contact the sensors of the X-ray imager. As the X-rays travel through the imaging volume, they can be affected by the properties of any material, such as a biological sample, within the imaging volume. Regions of the biological sample with differing degrees of radiodensity will permit differing amounts of X-rays to pass through those regions. These differing amounts will result in changes in the signal intensities detected by different areas of the X-ray imager sensors. As the rotatable imaging stage is moved around one or both of its orthogonal rotational axes, the locations of any radiodense regions of the biological sample relative to the locations of the X-ray source and X-ray imager will be changed. This allows for the recording of X-ray images with the X-ray imager that provide information about the radiopacity of the sample as detected from multiple perspectives.

The fluorescence excitation light source can be any device configured to emit electromagnetic radiation at an excitation wavelength capable of exciting a fluorescent material within the imaging volume. The fluorescent material can comprise a fluorophore or fluorescent dye. The fluorescence excitation light source is configured to illuminate the imaging volume, and any sample within, with radiation comprising this excitation wavelength. In some embodiments, the fluorescence excitation light source emits near-infrared light. In certain aspects, the illumination of the biological sample with near-infrared light is performed at one or more wavelengths of from about 650 nm to about 1400 nm. These wavelengths include, for example, about 700, 725, 750, 775, 800, 825, 850, 875, 900, 910, 920, 930, 940, 950, 960, 970, 980, 990, 1000, 1100, 1200, 1300, and 1400 nm. Sometimes these wavelengths are referred to as being in the NIR-I (between 750 and 1060 nm) and NIR-II (between 1000 nm and 1700 nm) wavelength regions.

Fluorophore methods utilize molecules that absorb light of one wavelength and emit light of a different wavelength. To utilize a visible image in combination with a fluorophore (e.g., an infrared or near-infrared fluorophore), care should be taken to ensure that the spectra of light variously absorbed, reflected, and emitted do not significantly overlap so as to confound differentiation of the components from each other and differentiation of the components from endogenous tissue material. Filter sets can be used in the optical system to isolate excitation wavelengths with optimized emission collection for corresponding imaging agents.

In certain aspects, the biological sample comprises a fluorescent dye. In one aspect, the fluorescent group is a near-infrared (NIR) fluorophore that emits in the range of between about 650 to about 1400 nm. Use of near-infrared fluorescence technology is advantageous in the methods herein as it substantially eliminates or reduces background from auto fluorescence of tissue. Another benefit to the near-IR fluorescent technology is that the scattered light from the excitation source is greatly reduced since the scattering intensity is proportional to the inverse fourth power of the wavelength. Low background fluorescence and low scattering result in a high signal to noise ratio, which is essential for highly sensitive detection. Furthermore, the optically transparent window in the near-IR region (650 nm to 990 nm) or NIR-II region (between about 1000 nm and 1400) in biological tissue makes NIR fluorescence a valuable technology for imaging and subcellular detection applications that require the transmission of light through biological components.

In certain aspects, the fluorescent group is preferably selected form the group consisting of IRDYE®800RS, IRDYE® 800CW, IRDYE® 800, ALEXA FLUOR® 660, ALEXA FLUOR® 680, ALEXA FLUOR® 700, ALEXA FLUOR® 750, ALEXA FLUOR® 790, Cy5, Cy5.5, Cy7, DY 676, DY680, DY682, and DY780 molecular marker. In certain aspects, the near infrared group is IRDYE® 800CW, IRDYE® 800, IRDYE® 700DX, IRDYE® 700, or Dynomic DY676 molecular marker.

In certain aspects, the fluorescent dye is contacted with the biological sample prior to excising the biological sample from the subject. For example, the dye can be injected or administered to the subject prior to surgery or after surgery. In certain aspects, the dye is conjugated to an antibody, ligand, or targeting moiety or molecule having an affinity to a tumor or recognizes a tumor antigen. In certain aspects, the fluorescent dye comprises a targeting moiety. In one aspect, the surgeon "paints" the tumor with the dye. In certain aspects, the fluorescent dye is contacted with the biological sample after excising the biological sample from the subject. In this manner, dye can be contacted to the tissue at the margins.

In some aspects, the targeting molecule or moiety is an antibody that binds an antigen such as a lung cancer cell surface antigen, a brain tumor cell surface antigen, a glioma cell surface antigen, a breast cancer cell surface antigen, an esophageal cancer cell surface antigen, a common epithelial cancer cell surface antigen, a common sarcoma cell surface antigen, or an osteosarcoma cell surface antigen.

Illumination sources can be mounted proximate to the imaging volume in order to illuminate the sample with white light, monochrome light, near-infrared light, fluorescence light, or other electromagnetic radiation. One or more white lights can be used to illuminate the imaging volume. In some embodiments, the illumination of the biological sample with visible light is performed at one or more wavelengths of about 380 nm to about 700 nm. These wavelengths include, for example, about 380, 390, 400, 425, 450, 475, 500, 525, 550, 575, 600, 625, 650, 675, or about 700 nm. These wavelengths can occur in combination, such as in broadband white light.

One or more cameras of the apparatus can have an actively or passively cooled heat exchanger to maintain imaging sensors at low temperatures. The imaging sensors can be charge coupled device imaging sensors. The cooling can prevent optical background noise such as darkness or blooming. Other approaches for improving camera sensitivity to compensate for low light levels of fluorescence can include imaging with a monochrome sensor, long exposure durations, and electronic noise suppression methods. Exemplary camera and optical components are described in U.S. Pat. Nos. 7,286,232, 8,220,415, and 8,851,017.

The rotatable imaging stage can comprise a transparent portion, such as a window. The window can be transparent at the working wavelengths for both reflective light and fluorescence imaging. The transparent portion can further be transparent to X-rays. To accommodate a large size sample, the window can be configured to a shape that is wider than either the projection size of the imaging volume or the footprint of the target sample. A circle on the window can be used to mark the border of a suggested imaging area.

The material of the transparent portion can be, for example, borosilicate-based glass, acrylic, or other transparent material. The surface could be treated or coated for optical or surface functional requirements. Non-limiting examples of these treatments include those providing anti-reflection, transparency, absorption, hydrophobic, or hydrophilic properties to the surface.

The rotatable imaging stage can further comprise one or more marks. The marks can be regularly spaced or irregularly spaced. The marks can be configured to provide reference scales to users of the apparatus. The marks can also provide references to a computer processor used to analyze and manipulate images recorded of the sample within the imaging volume. In some embodiments, the marks comprise a radiopaque material. The radiopaque material can comprise a polymer or a metal.

The devices and methods can utilize a computing apparatus that is programmed or otherwise configured to automate and/or regulate one or more steps of the methods or features of the devices provided herein. Some embodiments provide machine executable code in a non-transitory storage medium that, when executed by a computing apparatus, implements any of the methods or operates any of the devices described herein. In some embodiments, the computing apparatus operates the power source and/or pump control.

In some embodiments, the apparatus comprises a computer processor that can record images of the biological sample. The recorded images can be reflected light images captured by a camera configured to detect reflected light. In some embodiments, the reflected light is visible light. The recorded images can be fluorescence images captured by a camera configured to detect fluorescence emission light. In some embodiments, the same camera is configured to detect both reflected light and fluorescence emission light. The recorded images can be X-ray images captured by an X-ray imager. The X-ray images can be captured by a camera configured to detect light images presented on a display face of an X-ray flat panel detector. The computer processor can tag the recorded images with information related to the relative positions of one or more of cameras, imagers, detectors, or sensors, with respect to the rotatable imaging stage. The computer process can tag the recorded images with information related to the rotational position of the biological sample around either or both of a first and second orthogonal rotational axes. The locational and positional tags can use information determined by detecting the locations and orientations of one or more marks on the rotational imaging stage.

In some embodiments, the computer processor can control the rotation of the rotatable imaging stage. The rotation can be about one or both of the first and second orthogonal rotational axes. The rotation can occur simultaneously along with image recording. The rotation can be stopped during image recording. In some embodiments, the rotation is from one predetermined position to another. In some embodiments, the rotation is to a series of multiple different predetermined positions. The computer can record images captured in one or more channels or modalities at each position. As a non-limiting example, the computer can capture a reflected light image, a fluorescence image, and an X-ray image at each position that the rotatable imaging stage is moved to. The computer processor can rotate the imaging stage so that a transparent portion of the imaging stage is between the sample and one or more cameras, imagers, detectors, or sensors. Images or other information can then be recorded of the sample through the transparent portion of the imaging stage.

In some embodiments, the computer processer can construct models based on the recorded images. The models can be three-dimensional models. The models can comprise series of discrete images, each recorded as the rotatable imaging stage was at a different orientation relative to the apparatus element used in recording the images. The models can further comprise images constructed by interpolating information contained in discrete images. In some embodiments, the models are wireframe models created by translating two or more images into a polygonal mesh. The models can comprise surface information about the biological subject. The models can comprise tomographic information about the biological subject.

In some embodiments, the computer processer can render images produced from the constructed models. The rendered images can be identical to images recorded using the cameras, imagers, detectors, or sensors. The rendered images can be constructions based on information in the recorded images. The rendered images can contain images or information collected with one channel or modality. The rendered images can overlay images or information collected with two or more channels or modalities. As a non-limiting example, a rendered image can overlay reflected light information showing a visible light view of the biological sample, fluorescence information showing locations of fluorescing regions within the biological sample, and X-ray information showing locations of radiodense regions within the biological sample. Typically, when a rendered image overlays images or information from multiple channels, modalities, or models, the models are identically registered in three-dimensional space so that the image presents information for each modality as seen from a single viewpoint.

The apparatus can further comprise another energy source configured to deliver energy pulses into the imaging volume. In some embodiments, the energy source is a laser. In some embodiments, the energy source is a radio frequency transmitter. In some embodiments, the energy source is an ultrasound generator. In some embodiments, the energy pulses are non-ionizing laser pulses. In some embodiments, the energy pulses are radio frequency pulses. In some embodiments, the energy pulses are ultrasonic pulses.

The apparatus can further comprise an ultrasonic transducer array configured to detect ultrasound waves exiting the imaging volume and convert the waves into electrical signals. The energy pulses transmitted into the imaging volume can cause a biological sample within to absorb this time-varying energy, inducing the generation of acoustic waves that can be detected by the ultrasonic transducer array. Within the imaging volume, the ultrasonic transducer array is in contact with the biological sample via a coupling medium. The coupling medium can comprise water or gel to relay ultrasound waves. In some embodiments, the energy pulses are non-ionizing laser pulses and the ultrasonic transducer array can be used to record a photoacoustic image. In some embodiments, the energy pulses are radio frequency pulses and the ultrasonic transducer array can be used to record a thermoacoustic image. In some embodiments, the energy pulses are ultrasonic pulses, and the ultrasonic transducer array can be used to record an ultrasound image.

The apparatus can further comprise an interferometer configured for optical coherence tomography of the biological sample within the imaging volume. In some embodiments, the interferometer is a Michelson interferometer. The apparatus can further comprise a camera configured to detect electromagnetic radiation emitted from the imaging volume for optical coherence tomography of the biological sample.

Figure 2:
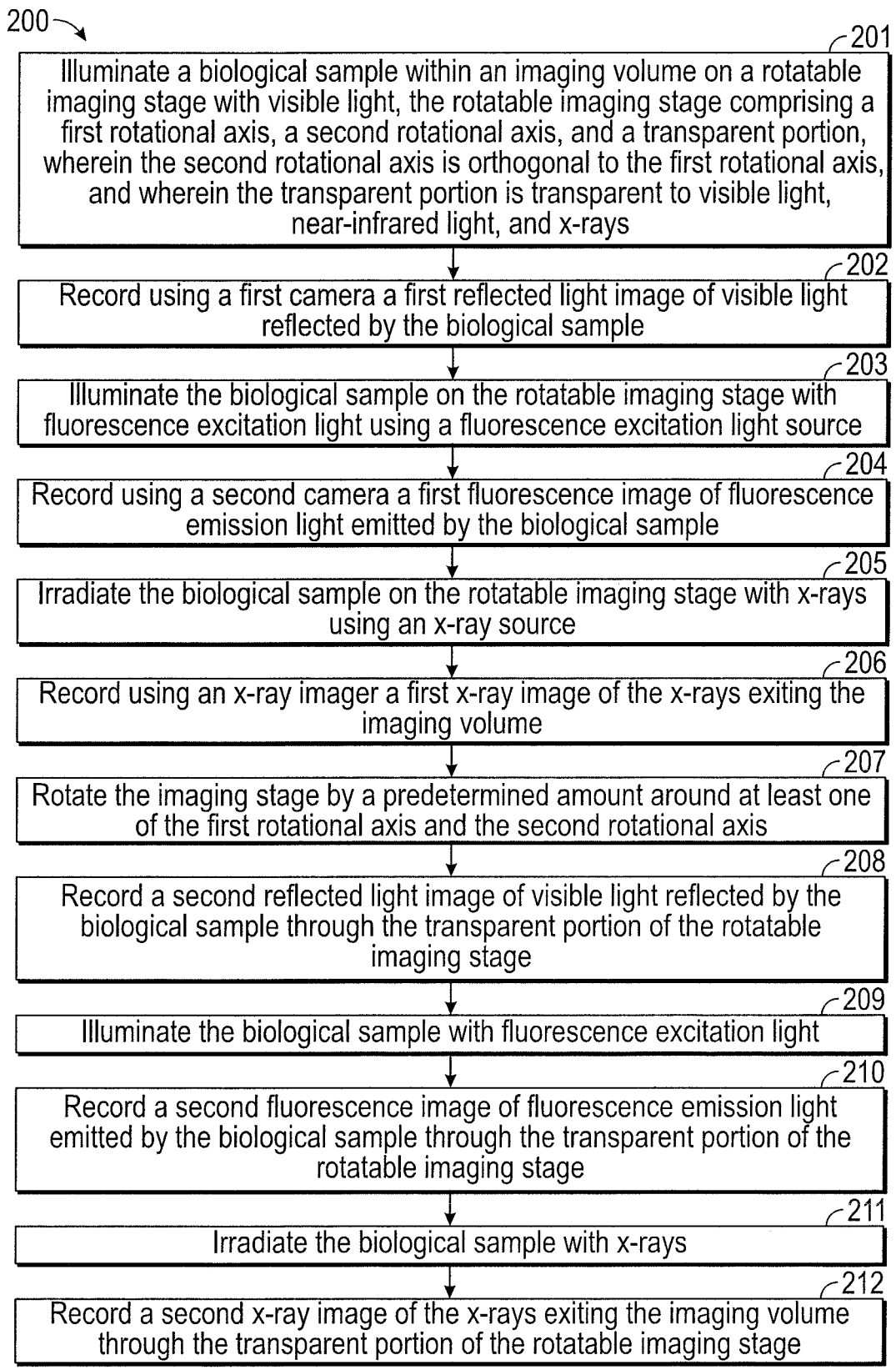
FIG. 2 is a flowchart of a process in accordance with an embodiment.

FIG. 2 presents a flowchart of a process 200 for imaging a biological sample with reflected visible light, fluorescence, and X-rays. In operation 201, a biological sample within an imaging volume on a rotatable imaging stage is illuminated with visible light, the rotatable imaging stage comprising a first rotational axis, a second rotational axis, and a transparent portion, wherein the second rotational axis is orthogonal to the first rotational axis, and wherein the transparent portion is transparent to visible light, near-infrared light, and x-rays. In operation 202, a first reflected light image of visible light reflected by the biological sample is recorded using a first camera. In operation 203, the biological sample on the rotatable imaging stage is illuminated with fluorescence excitation light using a fluorescence excitation light source. In operation 204, a first fluorescence image of fluorescence emission light emitted by the biological sample is recorded using a second camera. In operation 205, the biological sample on the rotatable imaging stage is irradiated with X-rays using an X-ray source. In operation 206, a first X-ray image of the X-rays exiting the imaging volume is recorded using an X-ray imager. In operation 207, the imaging stage is rotated by a predetermined amount around at least one of the first rotational axis and the second rotational axis. In operation 208, a second reflected light image of visible light reflected by the biological sample through the transparent portion of the rotatable imaging stage is recorded. In operation 209, the biological sample is illuminated with fluorescence excitation light. In operation 210, a second fluorescence image of fluorescence emission light emitted by the biological sample through the transparent portion of the rotatable imaging stage is recorded. In operation 211, the biological sample is irradiated with X-rays. In operation 212, a second X-ray image of the X-rays exiting the imaging volume through the transparent portion of the rotatable imaging stage is recorded.

In some embodiments, the method further comprises an operation to construct a three-dimensional reflected light model from the first and second reflected light images using a computer. In some embodiments, the method further comprises an operation to construct a three-dimensional fluorescence model from the first and second fluorescence images using the computer. In some embodiments, the method further comprises an operation to construct a three-dimensional X-ray model from the first and second X-ray images using a computer. In some embodiments, the method further comprises an operation to render an image produced from the reflected light model, the fluorescence model, and the X-ray model, wherein the reflected light model, the fluorescence model, and the X-ray model are identically registered in three-dimensional space.

The process presented in FIG. 2 can be carried out with an apparatus similar or identical to the one presented in FIG. 1. In some embodiments, the X-ray source 108 and the X-ray imager 109 are placed orthogonal to the optical imaging module 102. The center of the field-of-view of the X-ray imager 109 is on the same x-y plane as the field-of-view of the optical imaging module 102. In some embodiments, the X-ray source 108 and the X-ray imager 109 are placed at a defined angle along the z-axis of the imaging volume while maintaining the center of the field-of-view of the X-ray imager on the same x-y plane as the field-of-view of the optical imaging module 109. Therefore, if the optical module 102 is imaging the biological sample 106 at an angle of 0 degrees around the rotational axis of the imaging volume, the X-ray module can be used to record X-ray projection images of the biological sample at an angle of 90 degrees, 270 degrees, or any other defined angle around the rotational axis of the imaging volume. After the rotatable imaging stage has been rotated to a new orientation, and images of the biological sample have been recorded at this new orientation, registration of the images recorded with two or more modalities can be performed to provide co-localized and co-registered image information.

The process presented in FIG. 2 can be carried out with an apparatus in which the X-ray source 108 can irradiate the imaging volume with X-rays from the same direction as the direction of the optical module 102. In this case, the X-ray projection image recorded using the X-ray imager 109 is a view of the biological sample 106 from approximately the same angle as that of the image recorded using the optical module 102. In this embodiment, surface mapping images recorded using the optical module 102 will have registrations approximately identical to tomography images simultaneously recorded using the X-ray module. As a result, an operation involving subsequent co-localization and co-registration of the images recorded using different modalities can be eliminated.

In some embodiments, the method further comprises an operation to position the X-ray imager between the biological sample and the camera, wherein the X-ray imager is a flat panel detector, wherein the flat panel detector has a detection face and a display face, wherein the display face is opposite to the detection face, wherein the detection face is directed towards the biological sample, and wherein the display face is directed towards the camera. In some embodiments, the method further comprises an operation to irradiate the biological sample on the rotatable imaging stage with X-rays using an X-ray source, wherein the biological sample is positioned between the X-ray source and the flat panel detector, and wherein the X-ray source, the biological sample, the flat panel detector, and the first camera are collinear. In some embodiments, the method further comprises an operation to convert the X-rays detected by the detection face of the flat panel detector into a first X-ray image displayed on the display face of the flat panel detector.

In some embodiments, the method further comprises an operation to record using the first camera the first X-ray image displayed on the display face of the flat panel detector. In some embodiments, the method further comprises an operation to position the flat panel detector such that the flat panel detector is not between the biological sample and the camera. In some embodiments, the method further comprises an operation to rotate the imaging stage by a predetermined amount around at least of the first rotational axis and the second rotational axis. In some embodiments, the method further comprises an operation to position the flat panel detector between the biological sample and the camera. In some embodiments, the method further comprises an operation to irradiate the biological sample on the rotatable imaging stage with X-rays using an X-ray source. In some embodiments, the method further comprises an operation to converting the X-rays detected through the transparent portion of the rotatable imaging stage by the detection face of the flat panel detector into a second X-ray image displayed on the display face of the flat panel detector. In some embodiments, the method further comprises an operation to record using the first camera the second X-ray image displayed on the display face of the X-ray flat panel detector.

Figure 3:
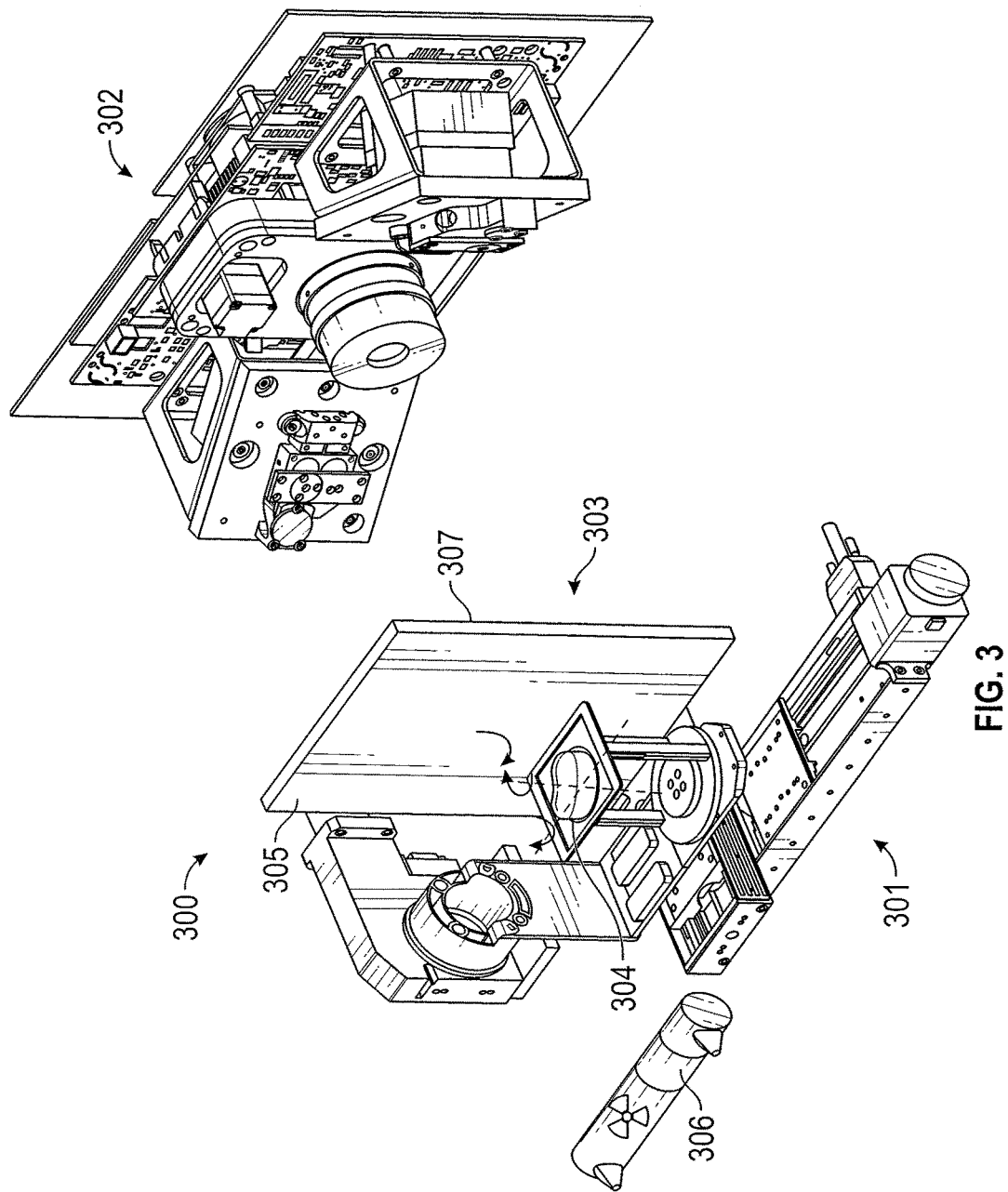
FIG. 3 is a perspective illustration of an imaging system with X-ray flat panel detector in accordance with an embodiment.

FIG. 3 illustrates one embodiment as a descriptive example. Shown is an apparatus 300 comprising a sample positioning module 301 and an optical imaging module 302. An X-ray flat panel detector 303 is positioned between a biological sample 304 and the optical imaging module 302. A detection face 305 of the flat panel detector 303 is contacted by X-rays generated by an X-ray source 306 that are not partially or completely blocked by regions of the biological sample 304. The flat panel detector 303 converts the X-rays detected by the detection face 305 into an X-ray image displayed on the display face 307 of the flat panel detector. The detection face 305 and the display face 307 are on opposite sides of the flat panel detector 303. The optical imaging module 302 can then be used to record the X-ray image displayed on the display face 303. To record images of the biological sample 304 with the optical imaging module 302 using imaging modalities other than X-rays, the flat panel detector 307 is repositioned so that it is not between the biological sample and the optical imaging module. In this way, the optical imaging module 302 can record images using, for example, one or both of a reflected visible light channel or a fluorescence channel. The flat panel detector 303 can be repeatedly moved from a first position enabling recording of X-ray images with the optical imaging module 302 as described, to a second position enabling recording of non-X-ray images with the optical imaging module 302

In certain aspects, the method provides illuminating a biological sample with visible light and capturing a plurality of first 2-D images using visible light. The method further includes illuminating the same or different biological sample with near infrared light and using the camera to capture a plurality of second 2-D images using infrared light. Preferably a single sample is used so that both illumination techniques can be used concurrently on a single sample without the visible light images changing the appearance of the near infrared images or vice versa.

In certain aspects, the plurality of 2-D first images are taken at different angles of the imaging stage rotated through a vertical axis. In certain other aspects, the plurality of 2-D first images are taken at different angles of the imaging stage rotated through a horizontal axis. In certain aspects, the plurality of 2-D second images are taken at different angles of the imaging stage rotated through a vertical axis. In certain aspects, the plurality of 2-D second images are taken at different angles of the imaging stage rotated through a horizontal axis.

Figure 4:
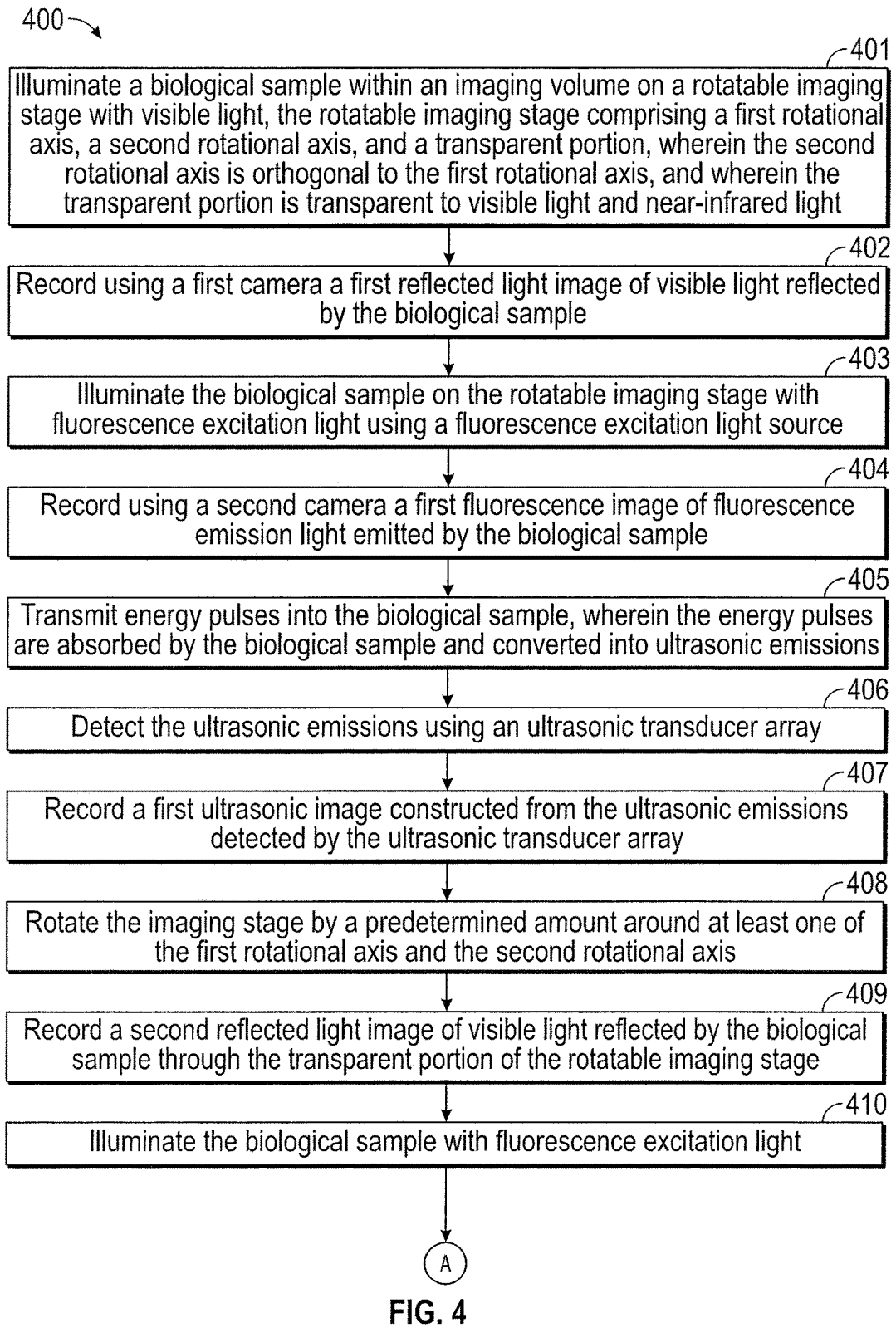
FIG. 4 is a flowchart of a process in accordance with an embodiment.
Figure 4:
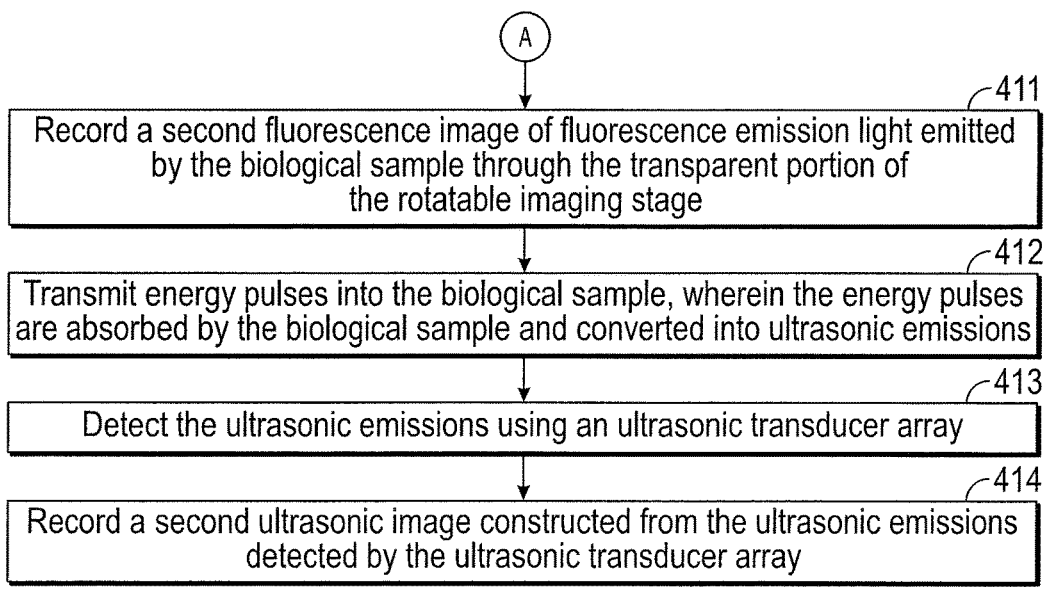

FIG. 4 presents a flowchart of a process 400 for imaging a biological sample with reflected visible light, fluorescence, and ultrasound. In operation 401, a biological sample within an imaging volume on a rotatable imaging stage is illuminated with visible light, the rotatable imaging stage comprising a first rotational axis, a second rotational axis, and a transparent portion, wherein the second rotational axis is orthogonal to the first rotational axis, and wherein the transparent portion is transparent to visible light and near-infrared light. In operation 402, a first reflected light image of visible light reflected by the biological sample is recorded using a first camera. In operation 403, the biological sample on the rotatable imaging stage is illuminated with fluorescence excitation light using a fluorescence excitation light source. In operation 404, a first fluorescence image of fluorescence emission light emitted by the biological sample is recorded using a second camera. In operation 405, energy pulses are transmitted into the biological sample, wherein the energy pulses are absorbed by the biological sample and converted into ultrasonic emissions. In operation 406, the ultrasonic emissions are detected using an ultrasonic transducer array. In operation 407, a first ultrasound image constructed from the ultrasonic emissions detected by the ultrasonic transducer array is recorded. In operation 408, the imaging stage is rotated by a predetermined amount around at least one of the first rotational axis and the second rotational axis. In operation 409, a second reflected light image of visible light reflected by the biological sample through the transparent portion of the rotatable imaging stage is recorded. In operation 410, the biological sample is illuminated with fluorescence excitation light. In operation 411, a second fluorescence image of fluorescence emission light emitted by the biological sample through the transparent portion of the rotatable imaging stage is recorded. In operation 412, energy pulses are transmitted into the biological sample, wherein the energy pulses are absorbed by the biological sample and converted into ultrasonic emissions. In operation 413, the ultrasonic emissions are detected using an ultrasonic transducer array. In operation 414, a second ultrasound image constructed from the ultrasonic emissions detected by the ultrasonic transducer array is recorded.

In some embodiments, the method further comprises an operation to construct a three-dimensional reflected light model from the first and second reflected light images using a computer. In some embodiments, the method further comprises an operation to construct a three-dimensional fluorescence model from the first and second fluorescence images using the computer. In some embodiments, the method further comprises an operation to construct a three-dimensional ultrasound model from the first and second ultrasound images using a computer. In some embodiments, the method further comprises an operation to render an image produced from the reflected light model, the fluorescence model, and the ultrasound model, wherein the reflected light model, the fluorescence model, and the ultrasound model are identically registered in three-dimensional space.

In some embodiments, the energy pulses are non-ionizing laser pulses, and the ultrasound image is a photoacoustic image. In some embodiments, the energy pulses are radio frequency pulses, and the ultrasound image is a thermoacoustic image. In some embodiments, the energy pulses are ultrasonic pulses.

Figure 5:
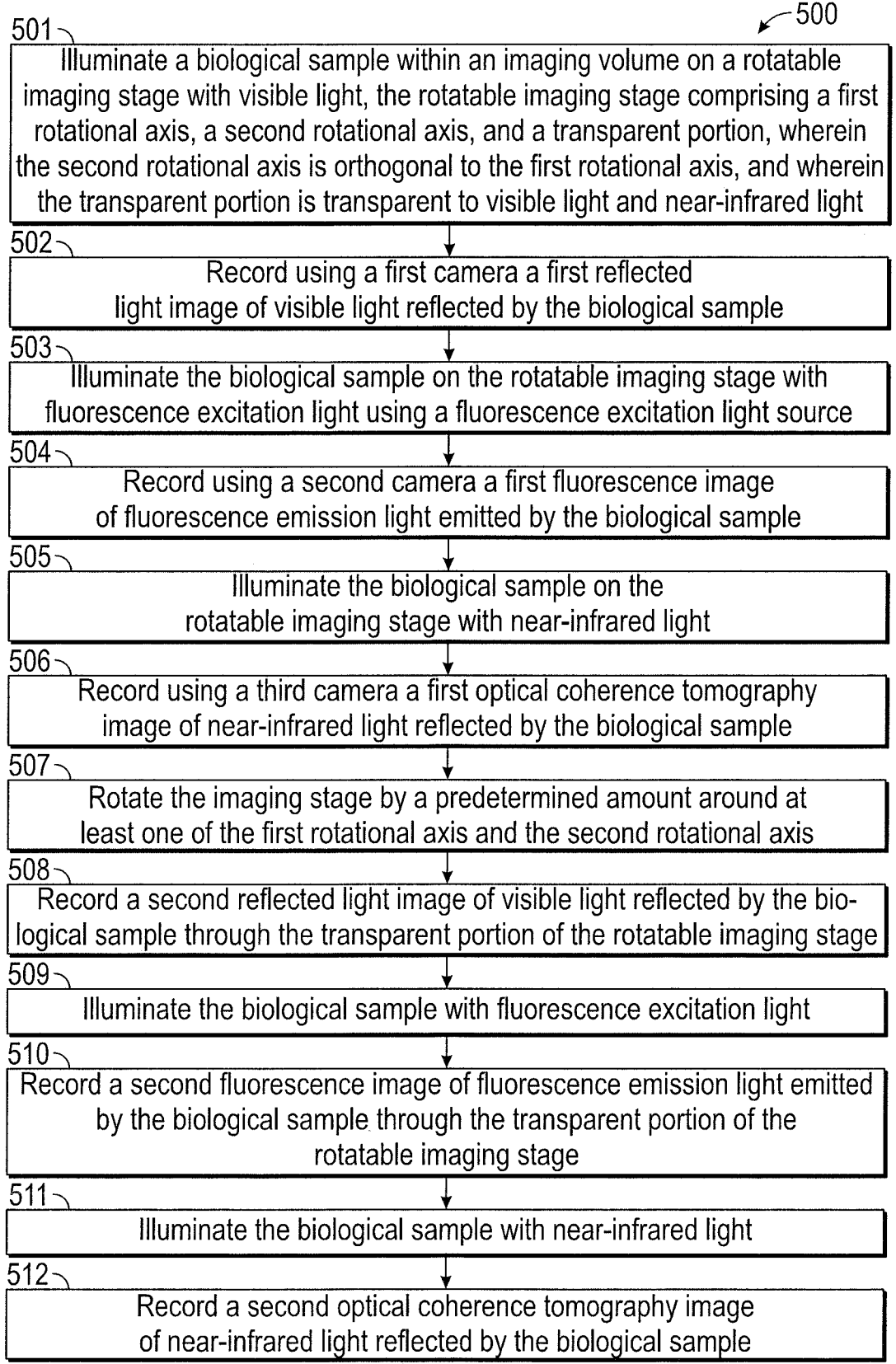
FIG. 5 is a flowchart of a process in accordance with an embodiment.

FIG. 5 presents a flowchart of a process 500 for imaging a biological sample with reflected visible light, fluorescence, and optical coherence tomography. In operation 501, a biological sample within an imaging volume on a rotatable imaging stage is illuminated with visible light, the rotatable imaging stage comprising a first rotational axis, a second rotational axis, and a transparent portion, wherein the second rotational axis is orthogonal to the first rotational axis, and wherein the transparent portion is transparent to visible light and near-infrared light. In operation 502, a first reflected light image of visible light reflected by the biological sample is recorded using a first camera. In operation 503, the biological sample on the rotatable imaging stage is illuminated with fluorescence excitation light using a fluorescence excitation light source. In operation 504, a first fluorescence image of fluorescence emission light emitted by the biological sample is recorded using a second camera. In operation 505, the biological sample on the rotatable imaging stage is illuminated with near-infrared light. In operation 506, a first optical coherence tomography image of near-infrared light reflected by the biological sample is recorded using a third camera. In operation 507, the imaging stage is rotated by a predetermined amount around at least one of the first rotational axis and the second rotational axis. In operation 508, a second reflected light image of visible light reflected by the biological sample through the transparent portion of the rotatable imaging stage is recorded. In operation 509, the biological sample is illuminated with fluorescence excitation light. In operation 510, a second fluorescence image of fluorescence emission light emitted by the biological sample through the transparent portion of the rotatable imaging stage is recorded. In operation 511, the biological sample is illuminated with near-infrared light. In operation 512, a second optical coherence tomography image of near-infrared light reflected by the biological sample is recorded.

In some embodiments, the method further comprises an operation to construct a three-dimensional reflected light model from the first and second reflected light images using a computer. In some embodiments, the method further comprises an operation to construct a three-dimensional fluorescence model from the first and second fluorescence images using the computer. In some embodiments, the method further comprises an operation to construct a three-dimensional optical coherence tomography model from the first and second optical coherence tomography images using a computer. In some embodiments, the method further comprises an operation to render an image produced from the reflected light model, the fluorescence model, and the optical coherence tomography model, wherein the reflected light model, the fluorescence model, and the optical coherence tomography model are identically registered in three-dimensional space.

In some embodiments, the method is used to image a biological sample with visible light and fluorescence emissions. Other imaging modalities that can be used with the method include X-ray imaging to visualize tissue density and radiopaque tissue inserts, photoacoustic imaging, optical coherence tomography, ultrasound imaging, positron emission tomography, single-photon emission computed tomography, Cherenkov luminescence imaging, bioluminescence imaging, fluorescence lifetime imaging, and spectroscopy.

Figure 6:
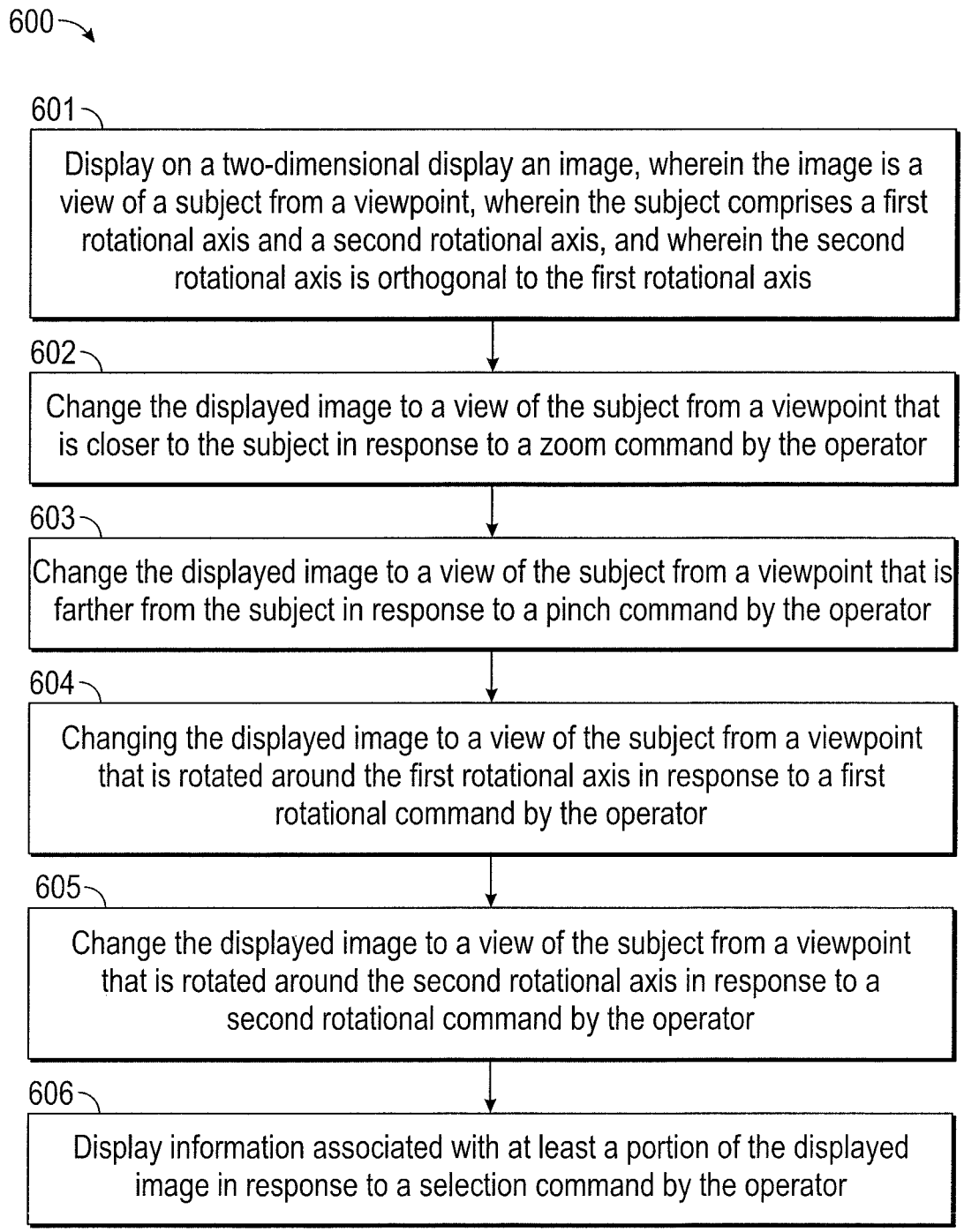
FIG. 6 is a flowchart of a process in accordance with an embodiment.

FIG. 6 presents a flowchart of a process 600 for presenting to an operator an image on a two-dimensional display. In operation 601, an image is displayed on a two-dimensional display, wherein the image is a view of a subject from a viewpoint, wherein the subject comprises a first rotational axis and a second rotational axis, and wherein the second rotational axis is orthogonal to the first rotational axis. The images from the viewpoint can be constructed by overlaying, melding, or otherwise combining reflected light, fluorescence, X-ray, ultrasound, and/or OCT images taken as described above. In operation 602, the displayed image is changed to a view of the subject from a viewpoint that is closer to the subject in response to a zoom command by the operator. In operation 603, the displayed image is changed to a view of the subject from a viewpoint that is farther from the subject in response to a pinch command by the operator. In operation 604, the displayed image is changed to a view of the subject from a viewpoint that is rotated around the first rotational axis in response to a first rotational command by the operator. In operation 605, the displayed image is changed to a view of the subject from a viewpoint that is rotated around the second rotational axis in response to a second rotational command by the operator. In operation 606, information associated with at least a portion of the displayed image is displayed in response to a selection command by the operator In some embodiments, the displayed image is produced from two or more three-dimensional models. The models can be, for example, any number of reflected light models, fluorescence models, X-ray models, ultrasound models, and optical coherence tomography models. Each model can be constructed from two or more images of the subject. The models are typically identically registered in three-dimensional space prior to producing the displayed image.

In some embodiments, one or more of the zoom, pinch, rotational, or selection commands are entered using key presses, control sticks, touch gestures, voice activation, or accelerometers. In some embodiments, the commands are entered using touch gestures. In some embodiments, the touch gestures are entered using a touch pen.

In a surgical workflow, a surgeon who operates a surgery only touches tools that are sterilized. In some surgical procedures, a technologist or other staff member assists a surgeon by helping to manipulate information presented on a display of any instrument. However, actions taken by the staff may not accurately or effectively accord with the verbal commands and requests from a surgeon. As a result, there can be a benefit to enabling surgeons to work with a display or instrument directly. Touching of instruments such as a computer, keyboards, display panels, or a cabinet imager may break the sterilization, though, and create contamination problems. The use of a sterile touch pen to operate a display or interface on a screen can therefore assist in maintaining a sterile environment in an operating room.

Figure 7:
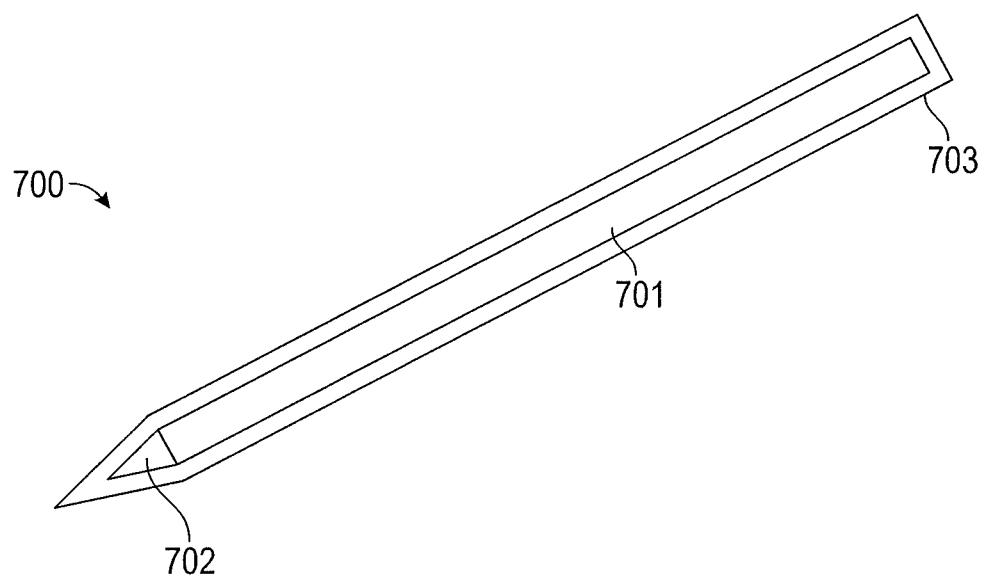
FIG. 7 is an illustration of a touch pen in accordance with an embodiment.

FIG. 7 illustrates one embodiment as a descriptive example. Shown is a touch pen 700 comprising a pen body 701 and a pen tip 702. The touch pen can also comprise a pen cover 703 that encloses the pen body 701 and the pen tip 702.

The pen body 701 can be made of disposable and pre-sterilized material intended for one-time or limited-time use. The pen body 701 can be or made of sterilizable material intended for repeated use with sterilization occurring prior to each use. In some embodiments, one or both of the pen body 701 and the pen tip 702 comprise a metal. In some embodiments, the metal is stainless steel. In some embodiments, the pen tip 702 is detachable from the pen body 701. The pen tip 702 can be made of disposable and pre-sterilized material intended for one-time or limited-time use. The touch pen can be enclosed in a pen cover 703 that is made of disposable and pre-sterilized material intended for one-time or limited-time use. In some embodiments, the pen body 701 and pen tip 702 are not sterile, but the pen cover 703 is sterile. In some embodiments, the touch pen can dispense ink from the pen tip. In some embodiments, the touch pen does not dispense ink from the pen tip.

In some embodiments, the touch pen has a touch tip at a first end and an ink tip at a second end that is opposite to the first end. The ink tip can be configured to dispense ink via, for example and without limitation, a ballpoint tip, a rollerball tip, a fountain tip, a felt tip, a small paint brush, or a spray dispenser. A clinician can use the touch pen to mark on the specimen directly. The mark can be used to indicate one or more areas of interest and to refer to areas that have been identified by the specimen imager and shown in the presentation display.

In some aspects, the pen dispenses visible ink. A clinician can then use the touch pen, without switching to another pen, to mark or put notes on a drape sheet, paper, towel, clothing article, gauze, or other material present in the operating room or specimen examination room. A clinician or other operator can also mark or put notes on a container, cage, cartridge, or other supporting material holding the excised specimen. Such notes are often kept with the gross specimen for later reference. The use of the touch pen for both operating the specimen imager and marking the sample related to the imaging process can provide an advantage by eliminating or reducing switching between a writing instrument and a touch instrument. This can in turn help to avoid contaminations, a particular concern for usage is in an operating room or other substantially sterile environment.

In some aspects, the pen dispenses ink that includes a fluorescent dye. The fluorescent ink can be visible or invisible. The fluorescent dye can be any of those described above, and can, for example, emit light in the NIR-I or NIR-II wavelength regions. Such NIR ink can be used to mark areas of interest on the biological sample or to provide annotations that can be visualized with NIR imaging. In some embodiments, the NIR ink has a different emission wavelength than that of fluorescent dyes used to label the sample tissue. In these cases the NIR ink can be read with NIR imaging, but will not interfere with readings of the staining of the sample. In some embodiments, the NIR ink is used to apply the staining to the sample. In these cases, the NIR ink can be selected to, for example, target disease tissues or cancer cells. Such usage can provide time and cost advantages by avoiding the systemic application of label agents to large areas of the sample. Directed application of NIR ink staining can also reduce the complexity of background signal variations across the specimen, in particular when the specimen comprises multiple tissue types. In some embodiments, the touch pen is preloaded with one or more fluorophores and targeting moieties.

The terms "about" and "approximately equal" are used herein to modify a numerical value and indicate a defined range around that value. If "X" is the value, "about X" or "approximately equal to X" generally indicates a value from 0.90X to 1.10X. Any reference to "about X" indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

Systems that incorporate the apparatus are also provided. Systems can include, for example, power supplies, power regulators, and other elements enabling the operation of the apparatus. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications, websites, and databases cited herein are hereby incorporated by reference in their entireties for all purposes.

What is claimed is:

1. An apparatus for imaging a biological sample, the apparatus comprising:
   a rotatable imaging stage adapted for supporting at least a portion of a biological sample within an imaging volume, the rotatable imaging stage comprising a first rotational axis and a second rotational axis, wherein the second rotational axis is orthogonal to the first rotational axis;
   an X-ray source configured to irradiate the imaging volume with X-rays;
   an X-ray imager configured to detect X-rays exiting the imaging volume;
   a fluorescence excitation light source configured to illuminate the imaging volume;
   a first camera configured to have a depth of focus within the imaging volume and to detect reflected light; and
   a second camera configured to have a depth of focus within the imaging volume and to detect fluorescence.

2. The apparatus of claim 1, wherein the imaging stage comprises a transparent portion that is transparent to visible light and near-infrared light.

3. The apparatus of claim 2, wherein the transparent portion is transparent to X-rays.

4. The apparatus of claim 2, wherein the transparent portion comprises glass or acrylic.

5. The apparatus of claim 1, wherein the imaging stage comprises a plurality of marks at predetermined intervals, wherein the marks comprise a radiopaque material.

6. The apparatus of claim 5, wherein the radiopaque material comprises a metal.

7. The apparatus of claim 1, wherein the X-ray source is an X-ray tube.

8. The apparatus of claim 1, wherein the X-ray imager is a flat panel detector.

9. The apparatus of claim 1, wherein the first camera is the second camera.

10. The apparatus of claim 1, further comprising
    a computer processor operatively connected with a machine-readable non-transitory medium embodying information indicative of instructions for causing the computer processor to perform operations comprising:
    recording reflected light images of the biological sample using the first camera;
    recording fluorescence images of the biological sample using the second camera;
    recording X-ray images of the biological sample using the X-ray imager; and
    rotating the rotatable imaging stage around at least one of the first rotational axis and the second rotational axis.

11. The apparatus of claim 10, wherein the operations further comprise:
    constructing a three-dimensional reflected light model from two or more reflected light images, wherein each of the two or more reflected light images is recorded with the rotatable imaging stage oriented in different positions around at least one of the first rotational axis and the second rotational axis;

constructing a three-dimensional fluorescence model from two or more fluorescence images, wherein each of the two or more fluorescence images is recorded with the rotatable imaging stage oriented in different positions around at least one of the first rotational axis and the second rotational axis;

constructing a three-dimensional X-ray model from two or more X-ray images, wherein each of the two or more X-ray images is recorded with the rotatable imaging stage oriented in different positions around at least one of the first rotational axis or the second rotational axis; and rendering an image produced from the reflected light model, the fluorescence model, and the X-ray model, wherein the reflected light model, the fluorescence model, and the X-ray model are identically registered in three-dimensional space.

12. The apparatus of claim 10, wherein the operations further comprise:

associating a first X-ray image of the X-ray images with a first reflected light image of the reflected light images and a first fluorescence image of the fluorescence images based on angles of the first and second rotational axes;

rendering a combined image based on the first X-ray, first reflected light, and first fluorescence images; and displaying the combined image to a user in series with other combined images.

13. A method for imaging a biological sample, the method comprising:

illuminating a biological sample within an imaging volume on a rotatable imaging stage with visible light, the rotatable imaging stage comprising a first rotational axis, a second rotational axis, and a transparent portion, wherein the second rotational axis is orthogonal to the first rotational axis, and wherein the transparent portion is transparent to visible light, near-infrared light, and X-rays;

recording using a first camera a first reflected light image of visible light reflected by the biological sample;

illuminating the biological sample on the rotatable imaging stage with fluorescence excitation light using a fluorescence excitation light source;

recording using a second camera a first fluorescence image of fluorescence emission light emitted by the biological sample;

irradiating the biological sample on the rotatable imaging stage with X-rays using an X-ray source;

recording using an X-ray imager a first X-ray image of the X-rays exiting the imaging volume;

rotating the imaging stage by a predetermined amount around at least one of the first rotational axis and the second rotational axis;

recording a second reflected light image of visible light reflected by the biological sample through the transparent portion of the rotatable imaging stage;

illuminating the biological sample with fluorescence excitation light;

recording a second fluorescence image of fluorescence emission light emitted by the biological sample through the transparent portion of the rotatable imaging stage;

irradiating the biological sample with X-rays; and recording a second X-ray image of the X-rays exiting the imaging volume through the transparent portion of the rotatable imaging stage.

14. The method of claim 13 further comprising:

constructing a three-dimensional reflected light model from the first and second reflected light images using a computer;

constructing a three-dimensional fluorescence model from the first and second fluorescence images using the computer;

constructing a three-dimensional X-ray model from the first and second X-ray images using the computer; and rendering an image produced from the reflected light model, the fluorescence model, and the X-ray model, wherein the reflected light model, the fluorescence model, and the X-ray model are identically registered in three-dimensional space.

15. The method of claim 13 further comprising:

positioning the X-ray imager between the biological sample and the first camera, wherein the X-ray imager is a flat panel detector, wherein the flat panel detector has a detection face and a display face, wherein the display face is opposite to the detection face, wherein the detection face is directed towards the biological sample, and wherein the display face is directed towards the first camera;

irradiating the biological sample on the rotatable imaging stage with X-rays using the X-ray source, wherein the biological sample is positioned between the X-ray source and the flat panel detector, and wherein the X-ray source, the biological sample, the flat panel detector, and the first camera are collinear;

converting the X-rays detected by the detection face of the flat panel detector into a first X-ray image displayed on the display face of the flat panel detector;

recording using the first camera the first X-ray image displayed on the display face of the flat panel detector;

positioning the flat panel detector such that the flat panel detector is not between the biological sample and the first camera;

rotating the imaging stage by a predetermined amount around at least of the first rotational axis and the second rotational axis;

positioning the flat panel detector between the biological sample and the first camera;

irradiating the biological sample on the rotatable imaging stage with X-rays using the X-ray source;

converting the X-rays detected through the transparent portion of the rotatable imaging stage by the detection face of the flat panel detector into a second X-ray image displayed on the display face of the flat panel detector; and recording using the first camera the second X-ray image displayed on the display face of the flat panel detector.

* * * * *